United States Patent
Pfahl

(12) 
(10) Patent No.: US 6,335,159 B1
(45) Date of Patent: Jan. 1, 2002

(54) RETINOIC ACID RECEPTOR ε(RARε)

(75) Inventor: Magnus Pfahl, Solana Beach, CA (US)

(73) Assignee: The Burnham Institute, La Jolla, CA (US)

( * ) Notice: Subject to any disclaimer, the term of this patent is extended or adjusted under 35 U.S.C. 154(b) by 0 days.

(21) Appl. No.: 08/003,497

(22) Filed: Jan. 12, 1993

Related U.S. Application Data

(63) Continuation of application No. 07/330,606, filed on Mar. 29, 1989, now abandoned, which is a continuation-in-part of application No. 07/221,171, filed on Jun. 16, 1988, now abandoned, and a continuation-in-part of application No. 07/266,529, filed on Nov. 3, 1988, now abandoned.

(51) Int. Cl.⁷ .................................................. G01N 33/564
(52) U.S. Cl. .......................... 435/6; 435/7.21; 435/7.23; 436/64; 436/501; 436/503; 436/813
(58) Field of Search ................................ 435/7.23, 7.21, 435/6; 436/64, 813, 501, 503

(56) References Cited

U.S. PATENT DOCUMENTS 5,223,606 A * 6/1993 Blaudin de Thé .......... 530/350
5,468,617 A   11/1995 De The et al. ................ 435/7.8

FOREIGN PATENT DOCUMENTS

EP        321362       6/1989

OTHER PUBLICATIONS de Thé, et al., *Nature*, vol. 330, No. 17, pp. 667–670, Dec. 1987.*

Brand, et al., "Identification of a Second Human Retinoic Acid Receptor", *Nature*, 332:850–853 (1988).

Petkovich, et al., "A Human Retinoic Acid Receptor Which Belongs to the Family of Nuclear Receptors", *Nature*, 330:444–450 (1987).

Giguere, et al., "Identification of a Receptor for the Morphogen Retinoic Acid", *Nature*, 330:624–629 (1987).

Evans, "The Steroid and Thyroid Hormone Receptor Superfamily", *Science*, 240:889–895 Figs. 2–5 (1988).

Umesono, "Retonoic Acid and Thyroid Hormone Induce Gene Expression Through a Common Responsive Element", *Nature*, 336:262–265 Figs. 2–4 (1988).

Benbrook, "A New Retinoic Acid Receptor Identified From a Hepatocellular Carcinoma", *Nature*, 333:669–672 Figs. 1–5 (1988).

Tizard, "Immunology, An Introduction", *Saunders Publ.*, 2 Ed:218–221 (1988).

Hudson, et al., "Practical Immunology", *Blackwell Sci. Publ.*, Alden Press, Oxford, p. 14 (1976).

* cited by examiner

*Primary Examiner*—Toni R. Scheiner
(74) *Attorney, Agent, or Firm*—Burns, Doane, Swecker & Mathis, L.L.P.

(57) ABSTRACT

This invention relates to substantially purified Retinoic Acid Receptor ε (RARε), having the amino acid sequence given in FIG. 1, and to the isolated nucleic acid encoding RARε. In addition, polypeptides comprising, and nucleic acids encoding, the DNA-binding and hormone-binding domain of the receptor are provided. Further, methods of detecting RARε and nucleic acids encoding RARε and its domains are provided.

1 Claim, 13 Drawing Sheets

FIG. 1

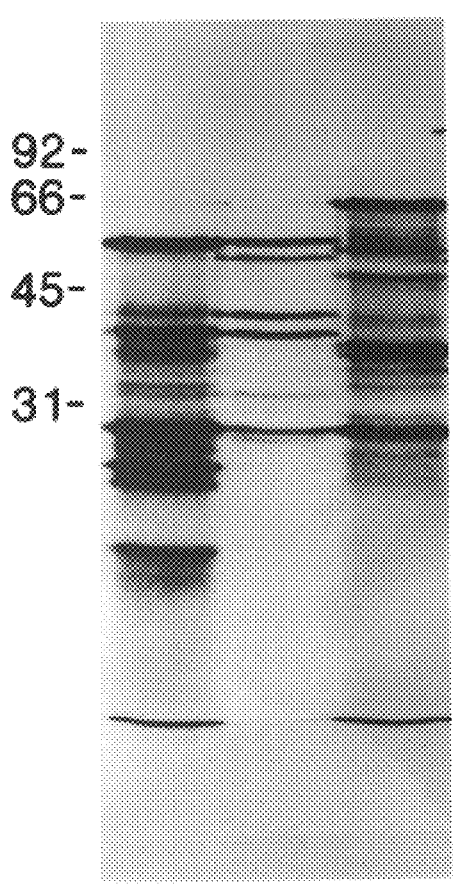
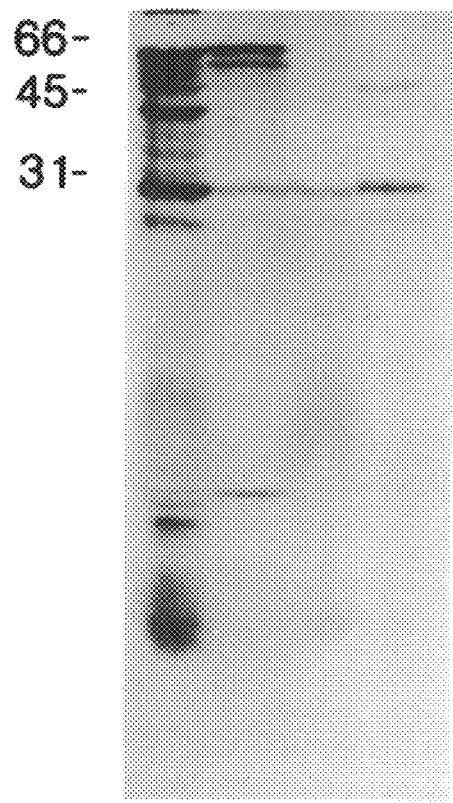
FIG. 2a
FIG. 2b

| CAT GENE | G17-2 |
| RECEPTOR | RAR-$E_2$ | RAR-$E_2$+TR$_\alpha$ |
| HORMONE | 0   $E_2$   0   $T_3$   $E_2$   $T_3$+$E_2$ |

RETINOIC ACID RECEPTOR ε(RARε)

This application is a continuation of application Ser. No. 07/330,606, filed Mar. 29, 1989 now abandoned, which is a continuation-in-part of application Ser. No. 07/221,171, now abandoned, filed Jun. 16, 1988, and a continuation-in-part of application Ser. No. 07/266,529, filed Nov. 3, 1988, now abandoned.

The subject invention was made pursuant to N.I.H. Grant No. RO1DK35083-04 and N.S.F. Grant No. DCB 8701336. The United States government may have certain rights in the invention.

BACKGROUND OF THE INVENTION

This invention relates to cell biology and more specifically to a novel receptor for retinoic acid.

Processes as diverse as growth, vision, and reproduction are dependent upon the presence of Vitamin A and its metabolites, which are termed retinoids. The molecular mechanisms which govern these diverse actions have remained unclear, however. Recently, the understanding of retinoid action has been advanced through the isolation of a specific nuclear receptor for retinoic acid, one of the physiologically active Vitamin A derivatives. See Petkovich et al., Nature 330:444–450 (1987); Giguere et al., Nature 330:624–629 (1987). This nuclear receptor, which is herein referred to as "RARα" and was previously referred to as "hRAR", is a member of the steroid-thyroid hormone receptor family.

Receptors of the steroid-thyroid hormone family are intracellular proteins which consist of discrete DNA-binding regions and ligand-binding regions. The DNA-binding domain of steroid hormone receptors and related proteins consists of a cystein-rich region that has been highly conserved and that has the potential to form two zinc-binding fingers. The ligand binding region is specific to the cognate ligand.

Retinoids are known to be essential for the normal function of many epithelial tissues. However, the reported tissue-specific expression of RARα is uncharacteristic for a molecule expected to be a major mediator of retinoid action in epithelial tissues. Because of their critical role in mediating metabolism and growth, it is important to determine other receptors mediating retinoid action. Knowledge of retinoid receptors permits the manipulation and control of metabolic effects resulting from retinoid action.

There thus exists a need for the identification and characterization of receptors mediating the retinoid response and methods of manipulating and detecting these receptors. The present invention satisfies this need and provides related advantages as well.

SUMMARY OF THE INVENTION

This invention relates to substantially purified Retinoic Acid Receptor ε (RARε), having the amino acid sequence given in FIG. 1, and to the isolated nucleic acid encoding RARε. In addition, polypeptides comprising, and nucleic acids encoding, the DNA-binding and hormone-binding domain of the receptor are provided. Further, methods of detecting RARε and nucleic acids encoding RARε and its domains are provided.

BRIEF DESCRIPTION OF THE DRAWINGS

FIG. 1 shows a comparison of the amino acid sequence encoded by the HBV-1 clone with amino acid sequences of other members of the nuclear receptor family, as described in Example I.

FIGS. 2a and 2b show the analysis of in-vitro-synthesized RARε protein, as described in Example 2.

DETAILED DESCRIPTION OF THE INVENTION

Figure 3:
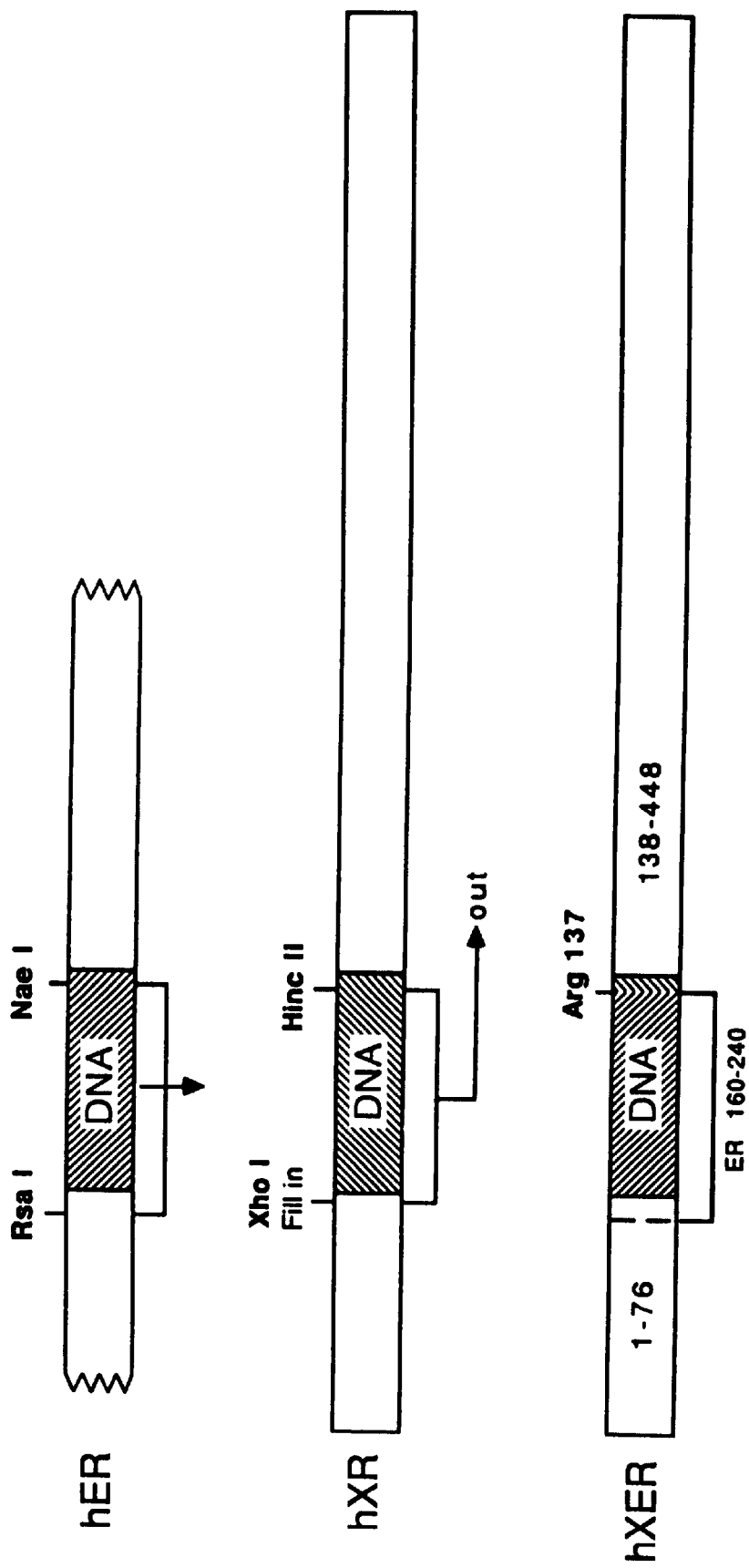
FIG. 3 shows "Finger Swap" from ER to RARε as described in Example III.

A new retinoic acid receptor, herein termed RARε, which is encoded by a cDNA clone from a human placental library, has been identified and characterized. RARε is a member of the steroid/thyroid hormone receptor family. A polypeptide having substantially the same function and amino acid sequence as RARε is also provided. As used herein "having substantially the same function" means modifications of the amino acid sequence which are neutral, improve, or lessen the function of RARε so long as the essential function is maintained. Thus, polypeptide analogs which have the activity of any portion of RARε, but which differ in amino acid content, are contemplated.

Polypeptides comprising the DNA-binding domain of RARε are provided. Polypeptides having substantially the same function and amino acid sequence as the DNA-binding domain are also provided These polypeptides can include not only the DNA-binding domain of RARε alone but also any portion of RARε which includes the DNA-binding domain. The polypeptides can be attached to other markers or polypeptides to utilize the DNA-binding characteristic. For example, the hormone binding domain of RARε receptor can be attached to the DNA-binding domain and transfected into cells. The cognate ligand of that particular receptor can then be added or limited to control transcription of a target gene.

Polypeptides comprising the hormone-binding domain, of RARε or polypeptides having substantially the same function and amino acid sequence are also provided. The ability to bind a ligand, for example retionic acid, is a contemplated function. However, the polypeptide does not include RARα. Like the DNA-binding domain, the hormone-binding domain can include not only the hormone-binding domain of RARε alone but also any portion of RARε which includes the hormone-binding domain of RARε. The polypeptide can be attached to other markers or polypeptides to utilize the hormone-binding characteristic. For example, the hormone-binding receptor can be attached to a known DNA-binding domain of another polypeptide and transfected into cells. A cognate ligand of the hormone-binding receptor, for example, retinoic acid, can then be added or limited to control transcription of a target gene.

Nucleic acids (for example, DNA, RNA, or cDNA) encoding the polypeptides of the invention are also provided. Vectors comprising these nucleic acids are also provided. Recombinant host (sells can be transformed with such a vector and used to express recombinant polypeptides. Such methods of recombinant expression are well known in the art, see Maniatis et al., Molecular Cloning: A Laboratory Manual (1982), which is herein incorporated by reference. Thus, recombinant polypeptides and the method of their production are also provided.

RARε is expressed at high levels in a number of epithelial-type tissues. It is also implicated in hepatocellular carcinoma development when its gene is activated by hepatitis B virus (HBV) integration in liver cells, where it is normally not expressed. A determination of its presence in malignant tissue is useful in elucidating the pathology of the tumor and in determining appropriate strategies of therapy.

Thus, the invention provides a method of diagnosing a tumor in a subject comprising detecting in a sample from the subject increased or decreased levels of RARε, increased or decreased levels of RARε indicating the presence of a tumor. For example, hepatocellular carcinoma can be detected since RARε expression can be altered in liver cells of a subject with hepatocellular carcinoma.

A method of diagnosing a tumor in a subject is also provided which comprises detecting in a sample from the subject a mutated form of RARε, the mutated RARε indicating the presence of a tumor. Any method of detecting polypeptides may be utilized, for example an immunoassay. By "mutated" is meant any variation of naturally occurring RARε. The mutation can result, for example, from the integration of a virus, a point mutation, a gene rearrangement, or gene amplification.

Cellular DNA surrounding a reported site of HBV integration in DNA derived from a human hepatocellular carcinoma has been reported to encode the first half of such a DNA-binding domain, Dejean et al., Nature 322:70–72 (1986). To isolate and characterize the receptor gene potentially activated by this HBV integration event, a synthetic oligonucleotide homologous to the cellular DNA sequence downstream of the HBV integration site was used to screen human cDNA libraries. A positive clone from a human placental library (clone HBV-1) was sequenced and revealed complete homology between nucleotides 500 and 649 with the putative exon sequence surrounding the HBV integration site of Dejean, supra.

The suggested open reading frame encodes a 448 amino acid protein of relative molecular mass ($M_r$) 50,000 (50 K), that contains the domains typical of members of the steroid-thyroid hormone receptor family. The cysteine-rich DNA-binding domain (C) is connected through a putative hinge region (domain D) with a ligand or hormone-binding domain (E). The amino-terminal region is short and contains only the (B) domain but no (A) domain. The (A) domain is typical for steroid hormone receptors but is not found in thyroid hormone receptors.

The hormone-binding domain (E) of the receptor oft present invention is 88% homologous with the previously described human retinoic acid receptor (RARα), Petkovich et al., supra; Giguere et al., supra. Domain D is also highly conserved and shows a 74% homology with RARε. The DNA-binding domain exhibits a 97% identity with RARα. A situation in which three colinear domains have been highly conserved has so fair only been observed between the two human thyroid hormone receptors encoded by the erbA-β and the erbA-T genes. In that case, it was shown that an 86% homology in the hormone-binding domain was sufficient to conserve ligand specificity, Benbrook et al., Science 238:788–791 (1987) which is incorporated herein by reference.

To further analyze the receptor of the present invention, the protein was synthesized in vitro by methods well known to those skilled in the art. RNA made in vitro containing the complete 5' untranslated region of the HBV-1 clone was efficiently translated in a rabbit reticulocyte lysate system. The largest protein banded slightly below the largest translation product of a thyroid hormone receptor, $hTR_\alpha$, on a denaturing polyacrylamide gel and clearly below the major oestrogen receptor, hER, a band (see FIG. 2), consistent with the predicted size of the protein encoded by the HBV-1 clone. The HBV-1 RNA was of a single size, and so the smaller proteins seen in the XR lane of FIG. 2 may represent translation products initiating at AUG codons within the coding sequence.

A "finger-swap" approach was used to determine the ligand-specificity of the novel receptor, using a modification related to an approach described by Green and Chambon, Nature 32;5:641–649 (1987), which is incorporated herein by reference. The DNA-binding domain (which presumably forms two zinc-binding fingers) of the novel receptor was exchanged with the DNA-binding domain of a receptor for which specific hormone-responsive DNA elements (HRE) have been identified. The hybrid receptor was then transfected into susceptible tissue-culture cells together with a reporter gene containing the relevant HRE. The effect of various potential activators of the novel receptor was measured from cells transiently transfected with both genes and grown in the presence and absence of the various ligands. The hER DNA-binding domain was used as the donor domain as outlined in FIG. 3. The resulting construct was confirmed by DNA sequencing. For further analysis of the construct, RNA of the new hybrid gene was translated in vitro. The major band migrated very similarly to the largest protein made from the wild-type gene, whereas other constructs which did not encode complete receptor proteins gave rise to smaller sized band (see FIG. 2b).

Figure 4:
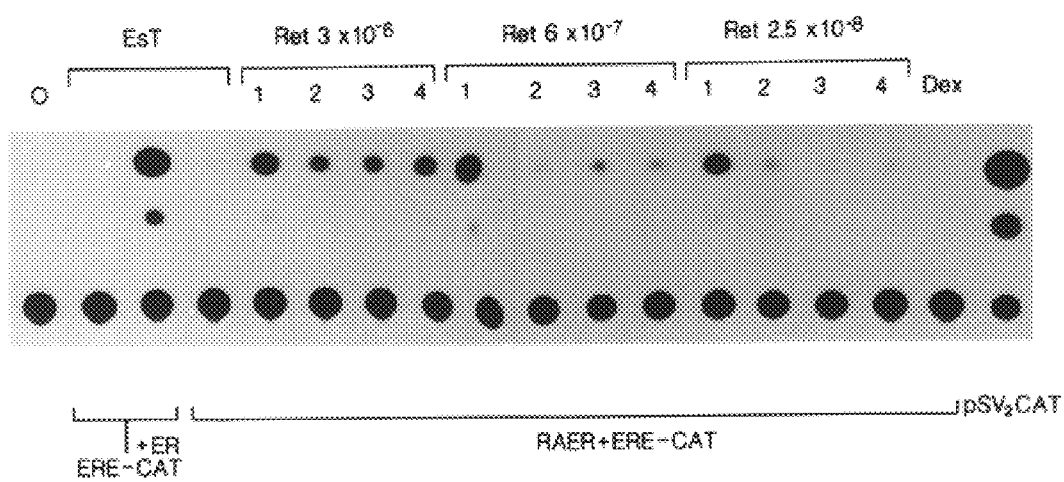
FIG. 4 shows RARε chimaeric protein activation of the transcription of an ERE-CAT reporter gene in the presence of retinoic acid as described in Example IV.

Results from transient co-transfection experiments using a CAT (chloramphenicol acetyl transferase) reporter gene linked to a promoter containing the estrogen-response element (ERE) are shown in FIG. 4. Only retinoic acid induced CAT gene expression strongly at a physiological concentration ($2.5 \times 10^{-8}$ M). The hybrid receptor was inactive in the presence of other unrelated, ligands (estradiol and dexamethasone). Other retinoids (retinol, retinal and retinyl-acetate) Showed some inducing effect only at high concentrations ($3 \times 10^{-6}$ M). The results indicate that the gene activated by HBV integration in a human hepatocellular. carcinoma, with similarity to steroid-thyroid hormone-like receptors, encodes a retinoic acid receptor.

Figure 5:
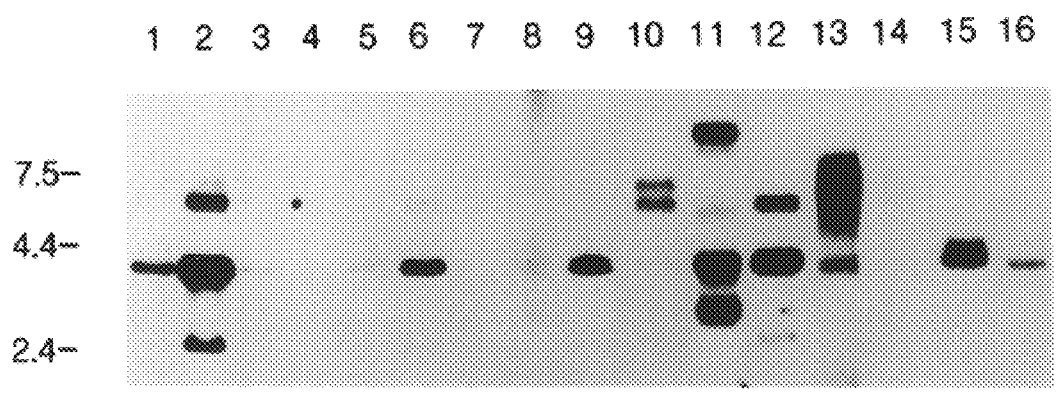
FIG. 5 shows tissue specific expression of RARε.

To obtain information on the physiological role of this new receptor, the tissue distribution of its mRNA was investigated (FIG. 5). Rat tissue was chosen because this species has been extensively used as a model system to establish tissue-responsiveness to retinoic acid. Strong expression was observed in brain (including pineal gland but not pituitary), pituitary gland, kidney, colon, uterus, ovary, testis, prostate gland, adrenal gland, and eye. The size of the transcript appears to vary ranging from 2.4 to 9.5 kb. The expression pattern is clearly distinct from previously reported RARα and shows (with the exception of brain) a considerable specificity for epithelial-type tissue including skin. Epithelial-type tissues are known to be most clearly affected by Vitamin A deficiencies, and a number (but not all) of symptoms of such deficiencies can be reversed by retinoic acid treatments. RARε mRNA appears to be present at considerably higher levels in epithelial-type tissue than $hTR_\alpha$ and hGR mRNAs, suggesting that the RARε is a major retinoic acid response mediator in epithelial-type tissue.

Vitamin A and other retinoids have been considered to be, and are used therapeutically as, anti-tumor drugs. Thus, RARε might contribute to tumor development when expressed erroneously in liver tissue, where it is normally silent (FIG. 5). Retinoids are known to maintain the proliferative state of epithelial cells. This type of cell proliferation, when induced in other types of tissue by erroneous RARε expression and the presence of retinoic acid, can lead to tumor development.

Gene probes which can hybridize with RARε nucleic acid can be prepared Basic techniques for preparing DNA oligonucleotide probes, as well as their screening by nucleic acid hybridization, are well known to those of ordinary skill in the art. See, for example, DNA CLONING: VOLUME I (D. M. Glover, ed. 1985); NUCLEIC ACID HYBRIDIZATION (B. D. Hames and S. J. Higgins eds. 1985): OLIGONUCLEOTIDE SYNTHESIS (M. J. Gate, ed. 1984); T. Maniatis et al., supra, all of which are incorporated herein by reference. For methods, see U.S. Pat. No. 4,358,535, which is also incorporated herein by reference.

For example, either oligonucleotides or cDNA or riboprobes derived from the cDNA can be used to probe the library and isolate the desired gene. The oligonucleotides are synthesized by any appropriate method, such as by the use of an automated DNA synthesizer. The particular nucleotide sequences selected are chosen so as to correspond to the codons encoding a known amino acid sequence from the protein. Since the genetic code is redundant, it will often be necessary to synthesize several oligonucleotides to cover all, or a reasonable number, of the possible nucleotide sequences which encode a particular region of the protein. Thus, it is generally preferred in selecting a region upon which to base the probes, that the region not contain amino acids whose codons are highly degenerate. In certain circumstances, on of skill in the art may find it desirable to prepare probes that are fairly long, and/or encompass regions of the amino acid sequence which would have a high degree of redundancy in corresponding nucleic acid sequences, particularly if this lengthy and/or redundant region is highly characteristic of the receptor protein. Probes covering the complete gene, or a substantial part of the genome, may also be appropriate, depending upon the expected degree of homology. It may also be desirable to use two or more probes, or sets of probes, each to different regions of the gene, in a single hybridization experiment. Automated oligonucleotide synthesis has made the preparation of large families of probe,s relatively straightforward. While the exact length of the probe employed is not critical, generally it is recognized in the art that probes from about 14 to about 20 bases are usually effective. Longer probes of about 25 to about 60 bases are also used.

The selected oligonucleotide probes are labeled with a marker, such as a radionucleotide or biotin, using standard procedures. The labeled set of probes is then used in the screening step, which consists of allowing the single-stranded probe to hybridize to isolated denatured DNA from the library, according to standard techniques. Either stringent or permissive hybridization conditions can be appropriate, depending upon several factors, such as the length of the probes and whether the probes are derived from the same species as the library or an evolutionarily close or distant species. The selection of the appropriate conditions is within the skill of the art. See generally, NUCLEIC ACID HYBRIDIZATION, supra. The basic requirement is that hybridization conditions be of sufficient stringency so that selective hybridization occurs; i.e., hybridization is due to a sufficient degree of nucleic acid homology (for example, at least about 75%), as opposed to nonspecific binding. Once a clone from the screened library has been identified by positive hybridization, it can be confirmed by restriction enzyme analysis and DNA sequencing that the particular library insert contains the desired gene.

Alternatively, a DNA coding sequence for the desired protein can be prepared synthetically from overlapping oligonucleotides whose sequence contains codons for the amino acid sequence of the protein. Such oligonucleotides are prepared by standard methods and assembled into a complete coding sequence. See, for example, Edge, (1981) Nature 292:756; Nambair et. al., (1984) Science 223:1299; Jay et al., (1984) J. Biol. Chem. 259:6311, all of which are incorporated herein by reference.

RARε can be used to produce antibodies, either polyclonal or monoclonal. If polyclonal antibodies are desired, purified RARε protein is used to immunize a selected mammal (for example, mouse, rabbit, goat, horse, etc.) and serum from the immunized animal is later collected and treated according to known procedures. Antisera containing polyclonal antibodies to a variety of antigens in addition to the RARε can be made substantially free of antibodies which are not anti-RARε specific by passing the composition through a column to which non-RARε protein has been bound. After washing, antibodies to the non-RARε proteins will bind to the column, whereas anti-RARε antibodies elute in the flow through.

Monoclonal anti-RARε antibodies can also be readily produced by one skilled in the art. The general methodology for making monoclonal antibodies by fusing myelomas and lymphocytes to form hybridomas is well known. Such cells are screened to determine whether they secrete the desired antibodies, and cain then be grown either in culture or in the peritoneal cavity of a mammal. Antibodies can also be created by techniques other than fusion, such as direct transformation or β-lymphocytes with oncogenic DNA, or transfection with Epstein-Barr virus, See, for example, M. Schreier et al., HYBRIDOMA TECHNIQUES (1980); Hammerling et al., MONOCLONAL ANTIBODIES AND T-CELL HYBRIDOMAS (1981); Kennett et al., MONOCLONAL ANTIBODIES (1980), which are incorporated herein by reference.

Antibodies specific to RARε have a number of uses. For example, they may be employed in an immunoassay to detect the presence of RARε. Detection of increased or decreased levels of RARε or a mutant form of RARε can be useful in diagnosing a tumor, for example, hepatocellular carcinoma. Various appropriate immunoassay formats are well known to those skilled in the art.

The invention also provides a method of detecting a ligand reactive Edith RARε or a polypeptide comprising the ligand-binding domain of RARε. The method comprises contacting a sample suspected of containing the ligand with RARε, or a polypeptide comprising the ligand-binding domain of RARε, or functional equivalents thereof, and detecting the binding to the ligand. By "functional equivalent" is meant any polypeptide, except RARε, having the ability to bind ligands reactive with RARε. Thus, minor changes in the amino acids or changes which increase or decrease the binding function are contemplated. Such changes would be expected to be found on the equivalent receptor in different species. In a preferred embodiment the ligand detected is retinoic acid.

Any immunoassay-type assay format can be used, substituting RARε or purified ligand-receptor for one or more of the antibodies. Since the ligands for the receptor are small molecules, preferably the assay is of the competitive type.

For example, the analyte being assayed is allowed to complex with the receptor by incubating the solid phase with a fluid sample suspected of containing the analyte. Radiolabeled analyte (other labels, such as fluorescent labeling are possible) is added to the sample. After the incubation period, the receptor-analyte complex is separated from the free analyte by binding the complex to a solid phase such as a Millipore filter. The filter solid phase is washed and analyte receptor complex bound to it is measured. The labeled analyte and the analyte in the sample will compete for binding to the receptor and the uptake of labeled analyte is inversely correlated to the amount of analyte in the test solution. Alternatively, the receptor can be coupled to a solid phase prior to contacting with the sample. In this assay, the receptor is coupled to a solid phase by means well known in the art. The solid phase may comprise any of a variety of porous materials, including various natural or synthetic materials, alone or in combination. Included among these are polysaccharides, for example, cellulose materials, such as paper and cellulose acetate; silica; inorganic materials such as deactivated alumina diatomaceous earth $MgSO_4$, or other inorganic finely divided material conveniently substantially uniformly dispersed in a porous polymer matrix with polymers such as vinyl chloride, vinyl chloride-propylene copolymer, and vinyl chloride-vinyl acetate copolymer; cloth, both naturally occurring, for example, cotton, and synthetic, for example, nylon cloth; porous gels, for example, silica gel, agarose, dextran, and gelatin; polymeric films, for example, polyacrylamide or the like. Another alternative is to remove the receptor-analyte complex from solution by allowing it to bind to an anti-receptor antibody which may itself be coupled to a solid support.

A method of detecting DNA reactive with RARε or a polypeptide comprising the DNA-binding domain of RARε is provided. The method comprises contacting DNA with RARε or a polypeptide comprising the DNA-binding domain of RARε, or a functional equivalents thereof, and detecting the binding to the DNA. Thus, specific DNA molecules, such as thyroid hormone responsive element (TRE), may be detected using, for example, a radiolabeled DNA-binding domain which binds to a specific DNA molecule. This detection can be useful, for example, in diagnosing genetic defects in receptor binding DNA sequences or in detecting DNA sequences which can be used in conjunction with RARε to regulate transcription.

A DNA sequence attached to RARε is also provided. The DNA sequence being a sequence which is responsive with RARε. By "attached" in meant chemically bound, for example, covalent or ionic. The sequence can occur in the promotor region just upstream from the promotor where the sequence, when properly attached by RARε, controls transcription of the coding regions downstream of the promoter. An example of a sequence responsive with RARε is thyroid hormone responsive element.

A second DNA sequence can be under the control of the promoter. The second DNA sequence can encode RNA which is translated into a desired polypeptide. Such expression can be carried out by placing a vector containing the second. DNA sequence under the control of the promoter and the DNA sequence responsive with RARε in proper orientation into an appropriate host: under polypeptide producing conditions. Appropriate vectors, hosts, DNA orientations, and polypeptide producing conditions are all well known to those skilled in the art, see for example, Maniatis et al., supra.

The recombinant host cells can be induced to produce the desired polypeptide by the introduction of RARε. The RARε can be endogenously produced by the host or may be produced by a transfected vector.

Additionally, transcription of DNA sequences normally activated by a retinoic acid receptor can be inhibited by adding nonactivated thyroid receptor to the cell. The thyroid receptor for RARε can be endogenously produced by the host or may be produced by a transfected vector. The retinoic acid receptor can be RARε or RARε and the thyroid receptor can be TRα or TRβ.

Finally, the invention provides a method of screening ligands for ligands which stimulate or inhibit RARε comprising adding the ligand to a recombinant host cell of the invention and observing the stimulation or inhibition of the polypeptide encoded by the second DNA sequence, an increase in the polypeptide indicating the stimulation of RARε and a decrease in the polypeptide indicating the inhibition of RARε. The conditions of the screening can be ascertained without undue experimentation by one skilled in the art.

Figure 6A:
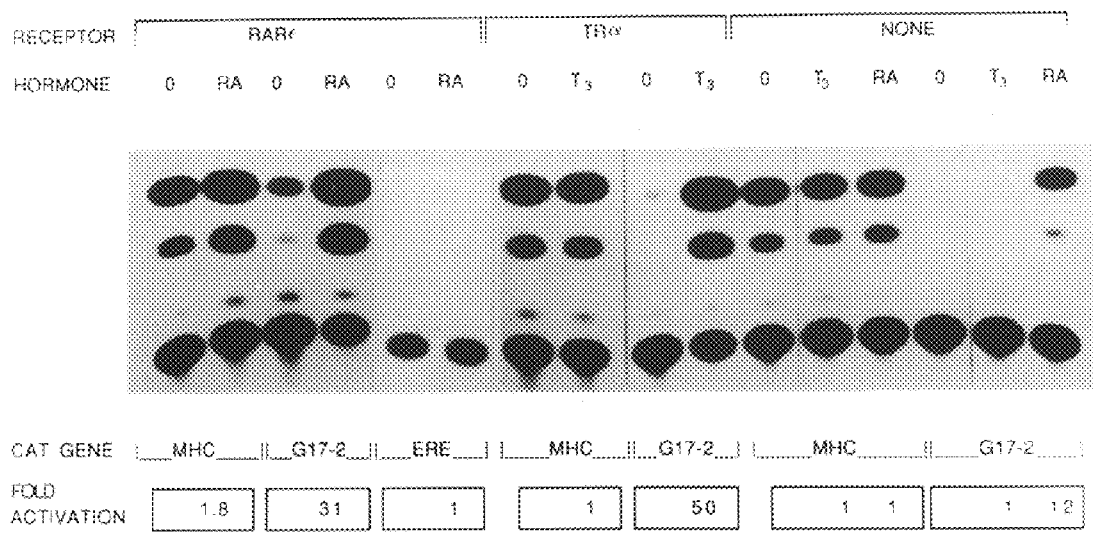
FIGS. 6a and 6b show RARε and the endogenous F9 cell RAR activate transcription from thyroid hormone responsive elements.
Figure 6B:
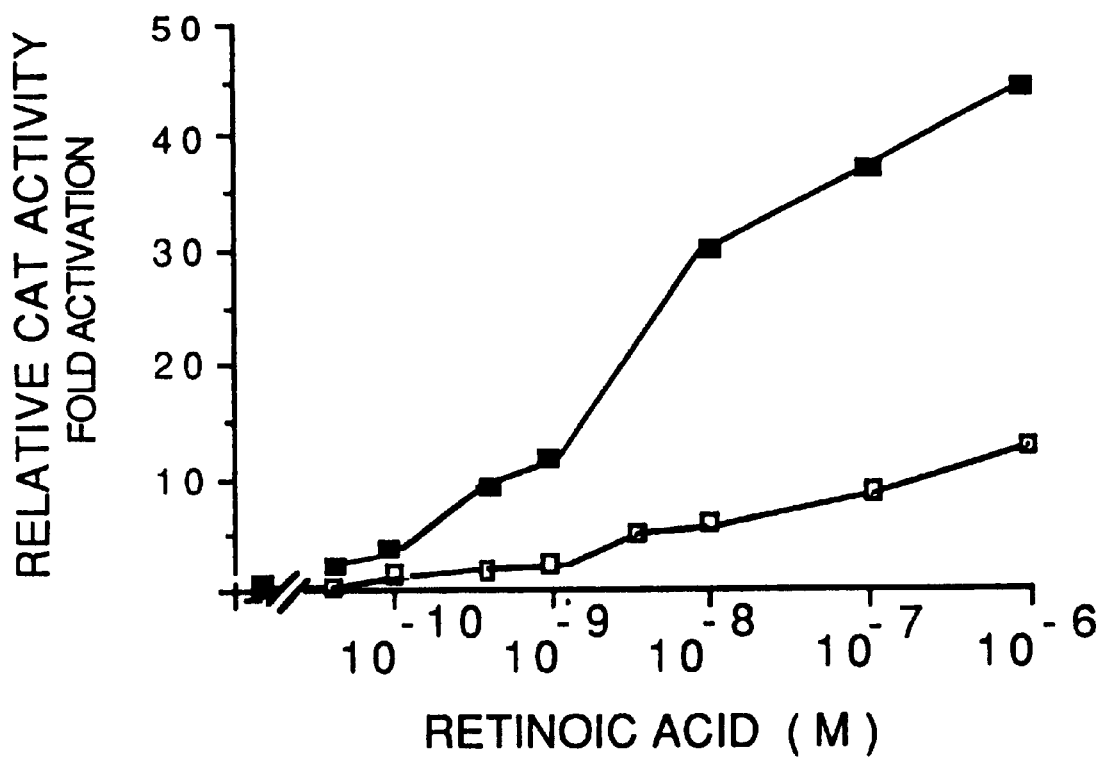

To define putative responsive elements for RARε the responsive elements of those receptors that showed high homology with RARε in the DNA binding domain were investigated (human estrogen receptor (ER) and the TRα and TRβ), described above and in Benbrook, D., et al., Nature, 333, 669–672 (1988) which is incorporated herein by reference. Two different TREs, one the natural myosin heavy chain (MHC) promoter TRE, Izumo, S., et al., Nature, 334, 539 (1988), and the other a synthetic TRE—G17-2—derived from the rat growth hormone promoter, Glass, C. K., et al., Cell, 54, 313–323 (1988), were chosen, both references are incorporated herein by reference. The estrogen responsive element (ERE) used here is derived from the vitellogenin gene, Klein-Hitpass, L., et al., Cell 46, 1053–1061 (1986). As a convenient assay system a cotransfection CAT assay (chloramphenicol transacetylase) was chosen. When. F9 teratocarcinoma cells were cotransfected with a RARε expression vector and TRE-CAT genes, a RA dependent induction of CAT activity was observed for both TRE constructs. In contrast, cotransfection experiments including ERE-tk-CAT and RARε did not reveal any significant induction of the indicator gene by RA (FIG. 6a). Upon induction, MHC and G17-2-TRE constructs yield very similar levels of CAT activity. However, the MHC-TRE-CAT gene is highly constitutive (high basal level activity) whereas the G17-2 construct functions as an ideal RA inducible gene in that we observe a low basal activity and a more than 30 fold induction of CAT activity by RA (FIG. 6a and b). Similar levels of induction were obtained with TRα. F9 cells have been established as a cellular model for RA dependent differentiation and to contain RAR transcripts. Whether the endogenous F9 RAR can also activate the TRE-CAT genes, by transfecting the receptor genes into F9 cells alone was investigated. A 12 fold induction in the presence of RA is observed for the G17-2 construct and no induction is seen in the presence of $T_3$, suggesting that F9 cells do not contain TR. The RA induction is, however, considerably lower than that observed in the presence of cotransfected RARε indicating that the endogenous RAR is limiting in concentration. The high basal level observed with the MHC construct prevents observation of a clear induction effect by the endogenous RAR. To investigate the RA concentration range necessary for RAR dependent. TRE activation, experiments using the G17-2 construct were carried out at RA concentrations between $3\times10^{-11}$ and $10^{-6}$ M (FIG. 6b). TRE dependent CAT activity can be induced by RARε or F9 RAR at the Preferred concentration of RA in the 0.1 nM range. These concentrations are well within the physiological range at which retinoids are known to function, Sporn, M. B., et, al., The retinoids, Vol. 1–2, Academic Press, Orlando, Fla. (1984), incorporated herein by reference.

Figure 7A:
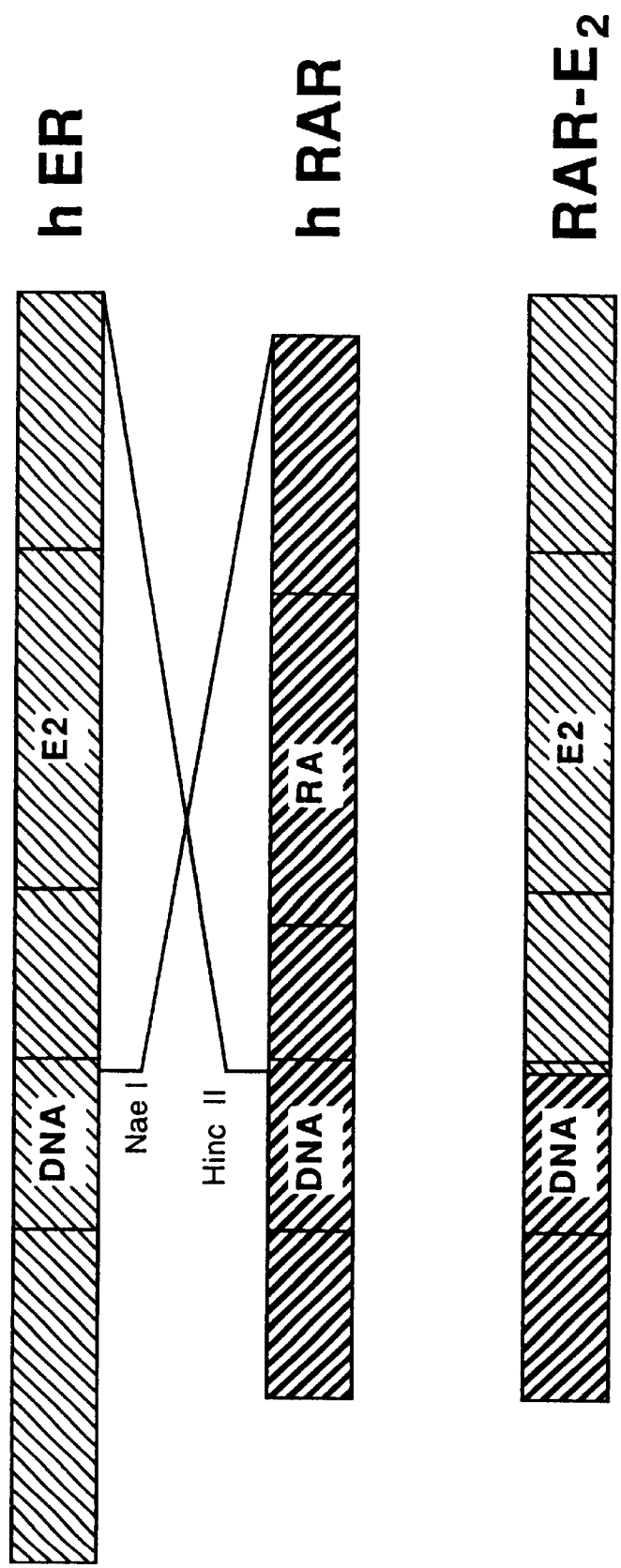
FIGS. 7a and 7b show a RAR-$E_2$ hybrid receptor confers estradiol inducibility to a TRE-CAT gene.
Figure 7B:
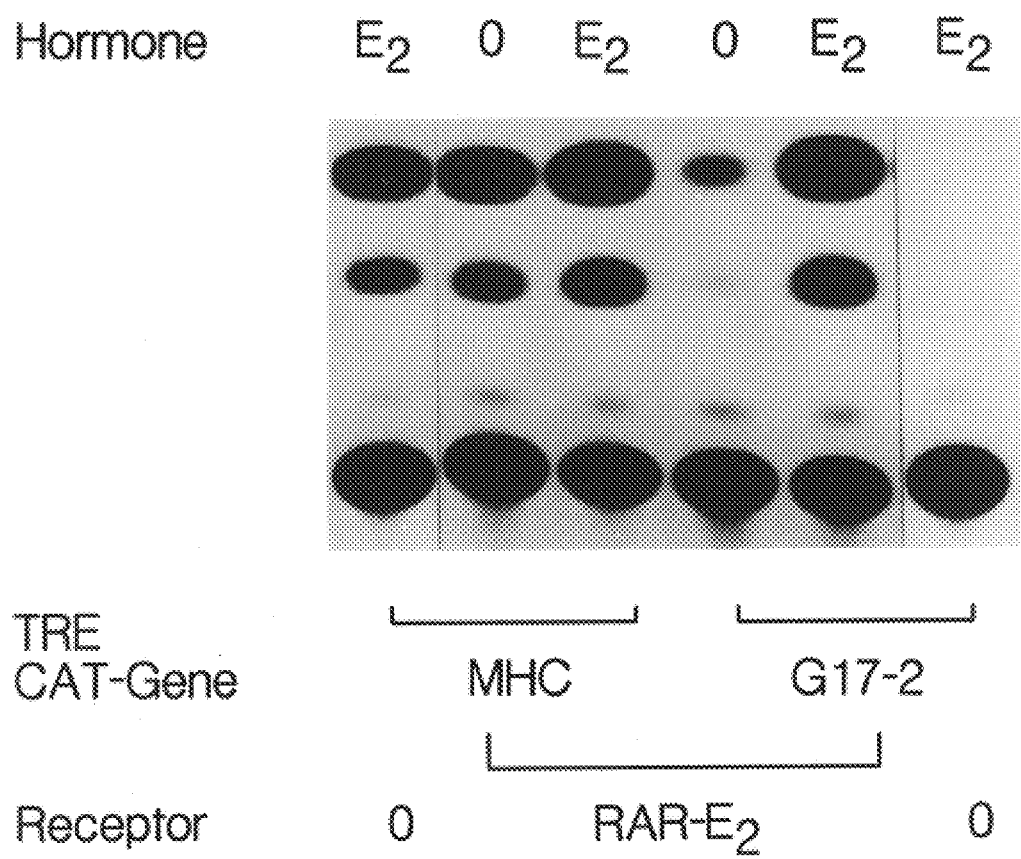

To map the domain of the retinoic acid receptor responsible for mediating the TRE-CAT gene activation, a hybrid receptor was constructed which contains the RARε DNA binding domain and the estrogen receptor hormone binding domain (FIG. 7a). It has been shown above that individual receptor domains can be exchanged to create receptors with novel specificities. When the hybrid receptor RAR-E$_2$ was cotransfected (FIG. 7a) with the TRE-CAT genes into F9 cells, induction of CAT activity in the presence of the hormone estradiol (E$_2$) was observed (FIG. 7b). Other hybrid receptors containing the ER DNA binding domain and the RARε hormone binding domain (see FIG. 10b) were unable to stimulate transcription from TRE-CAT genes. These data therefore define the DNA binding region of RARε as necessary for activating transcription from TREs in F9 cells.

Figure 8:
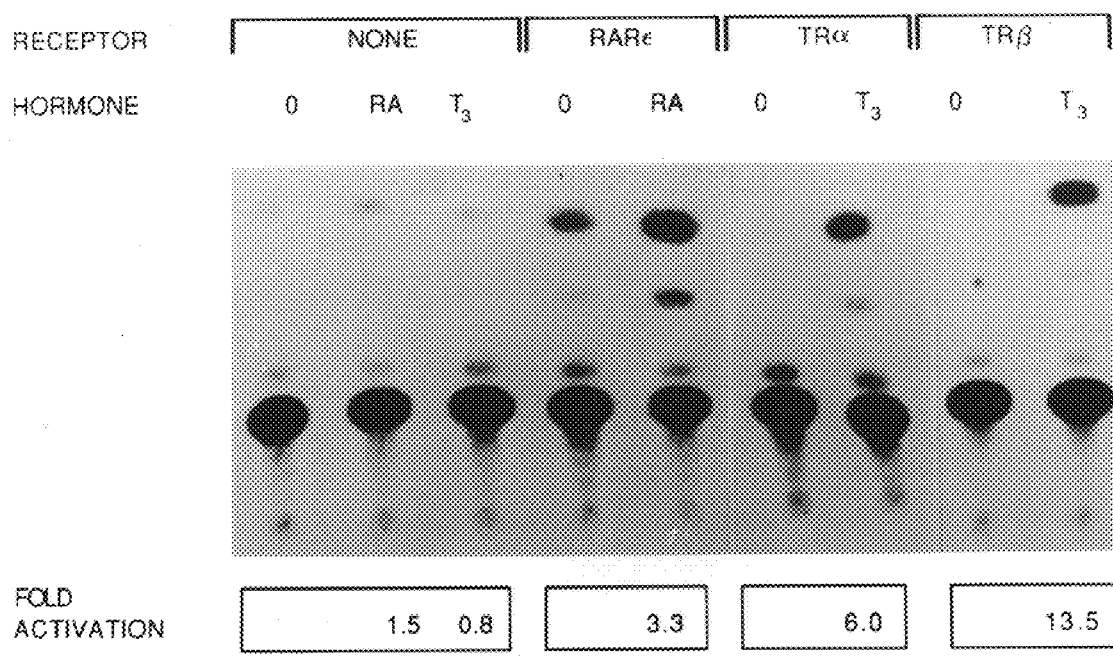
FIG. 8 shows RARε activates transcription from a thyroid hormone responsive element in CV-1 cells.

To ensure that RAR dependent TRE activation is not unique to one cell line the same experiments in CV-1 cells were carried out. The observations are similar to those obtained in the F9 cells. FIG. 8 depicts the results obtained with the G17-2 TRE CAT gene.

The data is, therefore, consistent with the assumption that TREs are highly efficient retinoic acid responsive elements, thus RA and T$_3$ likely modulate gene transcription via their nuclear receptors from a common family of responsive elements. One possible implication of this finding is that certain genes should be inducible by either hormone (T$_3$) or vitamin (RA) in cells containing both receptors. To zest this hypothesis and to investigate possible positive and/or negative interactions of TR and RAR, both receptors were cotransfected into the same cells together with a TRE-CAT gene. High CAT activity is observed in the presence of both ligands (T$_3$+RA). Approximately 70% of the maximal activity is observed when only T$_3$ is added. Surprisingly, no activity (or very low activity) is observed when only RA is added. These results were obtained in both F9 (FIG. 9a) and CV-1 cells (FIG. 9b), and suggest that in the presence of both receptors, TR alone controls the regulation of transcription from TREs. In the absence of T$_3$, TR prevents activation of TREs by RARs, while in the presence of T$_3$, TR activates and also allows positive cooperativity with RAR. The dominating regulatory effect can be carried out by both TRα and TRβ on both the RARε (FIG. 9) and the F9 endogenous RAR. Significant repression of RARε activity in F9 cells is observed between RARε: TRα ratios of 1:1 to 4:1.

Figure 10A:
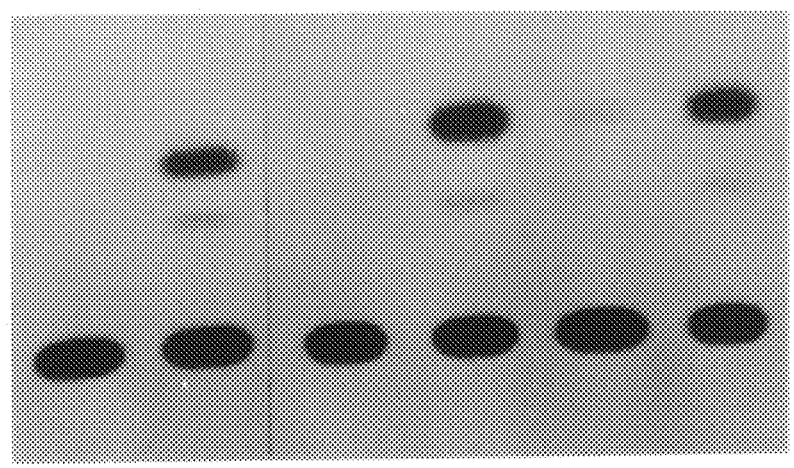
FIGS. 10a, 10b and 10c show RAR regions sensitive to TR repression by hybrid receptor analysis.
Figure 10B:
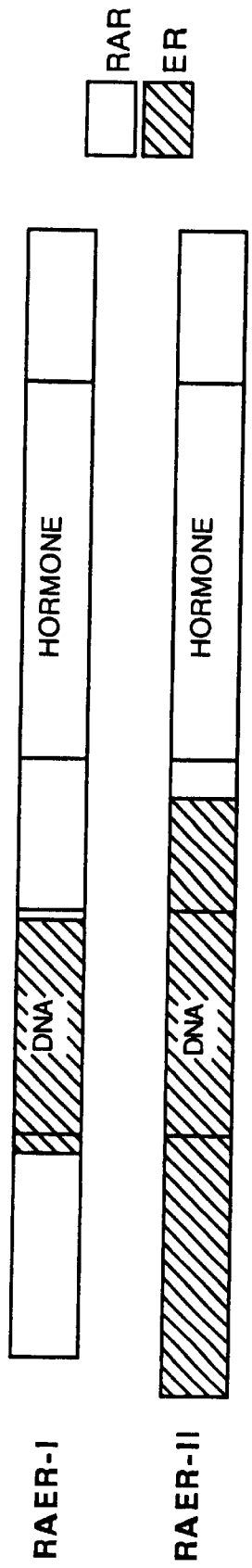
Figure 10C:
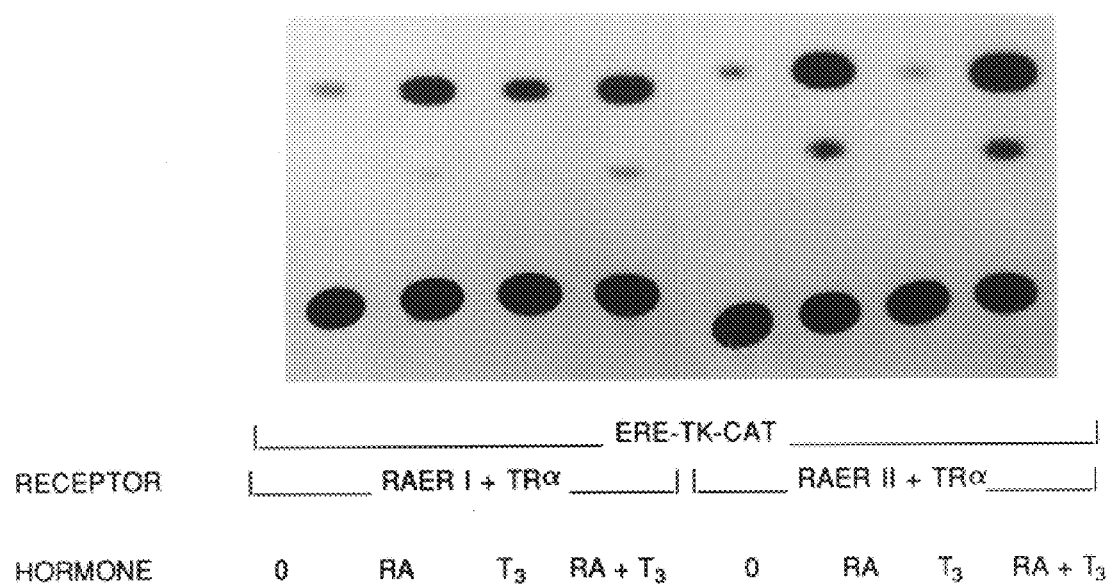

To define the region(s) of RAR sensitive to repression by thyroid hormone receptors a number of hybrid receptors were analyzed. The RAR-E$_2$ in Example VII, is inhibited by TRα (or TRβ) almost as efficiently as RARε in spite of the altered hormone specificity (FIG. 10a). The hybrid receptors RAER-I and RAER-II (FIG. 10b) which contain ER DNA binding domains and RARε hormone binding domains cannot be inhibited by TRs (FIG. 10c). In addition, glucocorticoid receptor cannot inhibit RAR activity. Thus, the repression of RAR activity by the nonactivated TR is mediated by specific interference with the DNA binding of RAR. The mechanistic details of the TR repressor mechanism still need to be elucidated; in particular, whether the receptors compete independently for the DNA binding site or whether an additional level of regulatory control by mutual protein-protein interaction exists. If the competition model applies, one would predict that TRα and TRβ both bind to TREs in the absence of ligand. This would be in agreement with reported findings that several steroid hormone receptors can bind specific DNA sequences in the absence of hormone. See, for example, Willmann, T., et al., Nature, 324, 688–691 (1986), incorporated herein by reference. Our observed repression is highly specific for RAR since the hybrid receptors activating an ERE-CAT gene are not significantly inhibited (FIG. 10c). The results differ from the in vitro binding data reported by Glass et al., Glass, C. K., et al., Cell, 54, 313–323 (1988), which suggest that TRs, in the presence of T$_3$, act as negative regulators of estrogen responsive genes., The following examples are intended to illustrate but not limit the invention.

EXAMPLE I

Nucleotide Sequence of RARε cDNA and Amino Acid Sequence of RARε Protein

Figure 1:
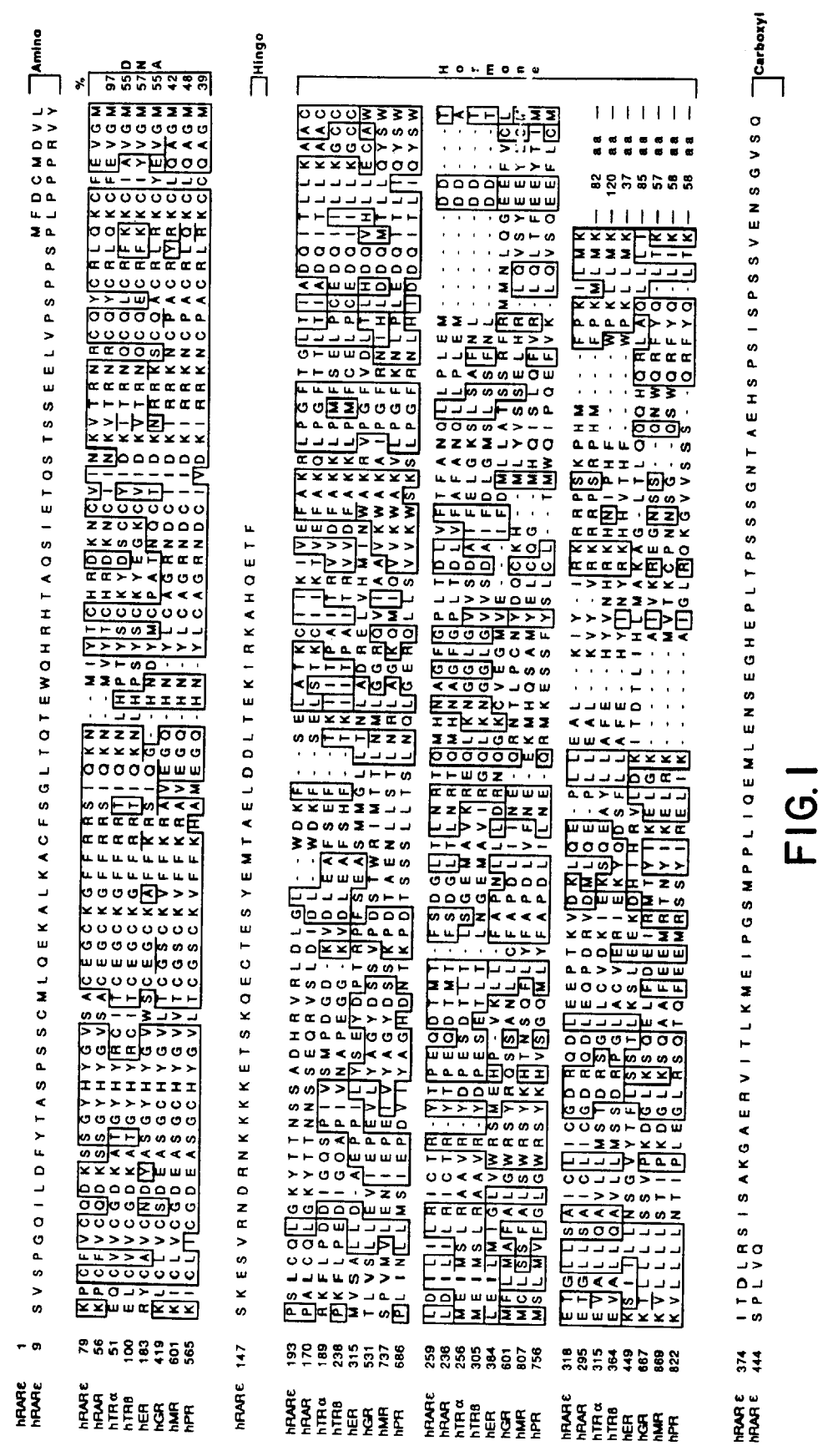

The complete amino acid sequence of the protein (RAR$_ε$) encoded by the HBV-1 clone is shown in FIG. 1. The sequence was deduced from the nucleotide sequence of a full-length cDNA clone isolated from a human placental library. The amino acid sequences of the DNA- and hormone-binding domains are compared with the same domains of other human proteins of this family: RAR, retinoic acid receptor Petkovich, et al., supra; and Giguere et al., supra; hTR and hTRβ, thyroid hormone receptor, Benbrook et al., supra; and Weinberger et al., Nature 324, 642–649 (1986); hER, estrogen receptor Green et al., Nature 320, 134–139 (1986) and Green et al., Science 231, 1150–1154 (1986); hGR, glucocorticoid receptor Weinberger et al., Nature 318, 610–612 (1985); hMR, mineralocorticoid receptor Arriza et al., Science 237, 268–275 (1987); hPR, progesterone receptor Misrahi et al., Comm. 143, 740–748 (1987). Percent homologies of RARε with the other receptor proteins in the DNA-binding domain are indicated. Amino acid residues are boxed when identical in three proteins or more. The highest homology with the RAR is seen in the DNA-binding domain where 97% of the amino acid residues are identical. This indicates that both proteins recognize similar if not identical DNA sequences. The DNA-binding domain also shows considerable homology to the human estrogen receptor (hER) (55%) and the α and β human thyroid hormone receptors (hTR), 55% and 57%, respectively (FIG. 1).

EXAMPLE II

Analysis of In-vitro-synthesized RARε Protein

In vitro-transcribed RNAs from clone HBV-1 were used to translate $^{35}$S-labeled RAR protein (lane XR) ; as controls, human estrogen receptor (lane ER), and human thyroid hormone receptor (lane T-1) were also synthesized using the same in vitro system, as shown in FIG. 2.

Analysis of tie protein from the RAR-ER hybrid gene is shown in FIG. 2. An in vitro transcription-translation system was used to analyze the protein encoded by the RAR-ER hybrid gene (lane XER) shown in FIG. 3. In vitro-made RARε (lane XR) and translation products from RAR constructs which did encode complete receptor proteins (lanes 1 and 2) served as controls.

A 1704 bp BamHI-DraI fragment from clone HBV-1 which contains a 304 bp 5' untranslated region, the complete open reading frame, and a 55 bp 3' untranslated region was ligated into the Bluescript vector (Stratagene, San Diego, Calif.), cut with BamHI and EccRV (clone B1-RAR). In vitro transcription and translation of the $^{35}$S-labeled RARε protein and the control proteins were carried out as described in Benbrook et al., supra, which, is incorporated herein by reference. Proteins were separated on a 15% SDS-acrylamide gel.

EXAMPLE III

"Finger-Swap" from ER to RAR$_ε$ Proteins

FIG. 3 presents a schematic representation given to illustrate the construction of an RARε-ER chimaeric gene. The brackets indicate the portions of the RARε (hXR) and ER DNA-binding domains used in the construct. These exchange regions contain the potential zinc-fingers of the DNA-binding domain.

The β1-RAR clone of Example I was cut with HindIII and ApaI, the ApaI ends were blunt-ended with mung-bean nuclease. The plasmid was then religated which resulted in a clone (RAR-9) in which the XhoI and HincII sites of the cloning box were deleted. To remove the DNA-binding region, RAR-9 (hXR) was digested with XhoI and HinchI which cut at unique sites. The staggered end of the XhoI sites was filled in. This resulted in a linearized plasmid from which the coding sequences of amino acids 77 through 136 and the first nucleotide of the Arg-137 codon of the RARε protein were deleted. A RsaI/NaeI fragment obtained from the hER cDNA clone, β1-ER, was ligated into the deleted RAR-9 clone. The β1-ER fragment encodes amino acid residues 168 through 240 and contains also; the first nucleotide of the Arg-241 codon of hER. Arg-137 of RAR and Arg-241 of ER are at the same positions in the two DNA-binding domains. The 5' end of the ER fragment encoders 13 amino acids more than were present on the excised RAR fragment. Constructs were analyzed by DNA sequencing. The clone with the described features is designated β1-RAER (XER). The major protein obtained from this clone by in vitro transcription-translation is indistinguishable in size from the largest RARε wild-type translation product (FIG. 4). To be able to express the RAER chimaeric protein in eukaryotic cells, the RAER gene was cut out with BamHI and KpnI (both sides in the cloning box) and ligated into the BglII and KpnI sites of the PECE eukaryotic expression vector, Ellis et al., Cell 45:721–732 (1986), incorporated herein by reference, which yielded clone PECE-RAER.

EXAMPLE IV

The RAER Chimaeric Protein Activated the Transcription of an ERA-CAT Reporter Gene in the Presence of a Retionic Acid HeLa cells were co-transfected with the PECE-RAER expression vector (RAER) and the oestrogen-responsive CAT gene (ERE-CAT) and grown in the presence of either $5 \times 10^{-9}$ M oestradiol (Est) or $5 \times 10^{-7}$ M dexamethasone (Dex) or the indicated molar concentrations of various retinoids (Ret):1, retinoic acid; 2, retinol; 3, retinal; 4, retinyl-acetate (see FIG. 4). As a control, cells were treated with calcium phosphate or were transfected with the constitutive pSV2CAT vector. As further controls, cells were also transfected with ERE-CAT and ERE-CAT plus the oestrogen receptor (ER) expression vector pckR2ER and grown in the presence of Est.

HeLa cells ($1.5 \times 10^6$ per dish) were transfected using calcium phosphate, Wigler et al., Cell 11, 223–232 (1977) which is incorporated herein by reference, with 5 µg of the expression vectors PECE-RAER or pckR2ER and 20 µg of the ERE-CAT vector or the pSV2CAT vector. After 5 hours, cells were shocked with 10% glycerol for 2 min. Eighteen hours after the start of transfection, steroid hormones or retinoids were added to the medium and cells were incubated for a further 24 hours before harvesting. CAT activity in cell extracts was determined as described by Gormon et al., Biol 2, 1044–1051 (1982), herein incorporated by reference.

EXAMPLE V

Tissue-Specific Expression of RARε

Northern blot analyses were performed with RNA (20 µg per lane) extracted from different rat tissues. Lane 1, brain; lane 2, pituitary; lane 3, atrium; lane 4, lung; lane 5, diaphragm; lane 6, kidney; lane 7, liver; lane 8, spleen; lane 9, colon; lane 10, uterus; lane 11, ovary; lane 12, testis; lane 13, prostate; lane 14, seminal vesicle; lane 15, adrenal; lane 16, eye (see FIG. 5). Markers on the side are in kb.

The quanidine isothyocyanate method of Maniatis et al., Molecular Cloning!, supra, which is incorporated herein by reference, was used to isolate RNA from tissues extracted from adult BK1: (SD) rats. Northern blots were prepared from 1% formaldehyde-agarose gels containing 20 µg RNA per lane, prehybridized at 42° C. overnight in 50% formamide, 5×SSPE (1×SSPE is 0.18 M NaCl, 10 mM NaPO$_4$, pH 7.7 1 mM EDTA), 5×Denhardt's reagent, 0.1% SDS, and 250 µg/ml$^{-1}$ sheared salmon sperm DNA. Hybridizations were at 42° C. in 50% formamide, 5×SSPE, 1×Denhardt's reagent, 0.1% SDS, 100 µg/ml$^{-1}$ sheared salmon sperm DNA, and 20 ng/ml$^{-1}$ of probe 1 for all lanes except 10, 12, 13, and 14 for which $2 \times 10^6$ cpm/ml of probe 2 was used. Probe I was labeled by nick-translating the β1-RAR whole plasmid ($10^8$ cpm/µg$^{-1}$) and probe 2 consisted of an EcoRI-SphI fragment of the 5' end of RAR labeled with Klenow using random oligonucleotides as primers ($10^9$ cpm/µg$^{-1}$). The blots were washed 3 times in 2×SSC and 0.1% SDS at room temperature for 20 minutes and twice in 5×SSPE, 1×Denhardt's, and 0.1% SDS at 60° C. for 1 hour. X-ray negatives were exposed to the blots for 16 hours.

EXAMPLE VI

RARε and the Endogenous F9 Cell RAR Activate Transcription from Thyroid Hormone Responsive Elements F9 cells were cotransfected with 5 µg of the expression vectors PECE-RARε or PECE-TRα and 20 µg of the reporter plasmids G17-2 CAT or MHC-CAT. As a control, cells were also transfected with the reporter plasmids only. The G17-2 CAT construct contains three copies of a synthetic TRE derived from the rat GH gene, Glass, C. K., et al., supra, incorporated herein by reference. The MHC construct contains nucleotides −163 to −81 upstream of the CAP site of the rat αMHC gene, Izumo,; S., et al., supra. Fold activation is expressed as the ratio of relative CAT activity after hormone induction to relative CAT activity without hormone induction. The mean of at least three experiments is given in FIG. 6(a). Ligand dependant activation of RARε and the endogenous F9 cell RAR is shown in FIG. 6(b). F9 cells were cotransfected with 5 µg of PECE-RARε and 20 µg of G17-2 CAT (■—■) or with 20 µg of the expression vector alone (□—□). Indicated amounts of hormones were added 24 hours after transfection.

2×10⁶ F9 cells were cultured as monolayer on gelatin-coated dishes in alpha-MEM (GIBCO, Santa Clara, Calif.), supplemented by 20% fetal calf serum (FCS), glutamine: and nucleosides as described in Grover, A., et al., J. Cell Biol. 96, 1690–1996 (1983) which is incorporated herein by reference. Two to five hours before transfection, cells were fed the above medium containing charcoal-treated FCS. Twenty-four hours after transfection, cells were fed with charcoal treated medium together with the appropriate amount of hormone (final hormone concentrations $5 \times 10^{-8}$ M). Forty-eight hours after transfection, cells were harvested, lysed and assayed as described by Gorman, C. M., et al., Mol. & Cell Biol. 2, 1044–1051 (1982), incorporated herein by reference. For accurate determinations of chloramphenicol acetylation, the separated reaction products were cut out from silica plates and quantified in a scintillation counter. Plasmid constructions: PECE-RARε was obtained by cloning a Ban HI-EcoR1 fragment (that contained the complete coding region of RARε) from clone B1-RAR, see above, (B1 stands for Bluescript; Stratagene Cloning Systems, San Diego, Calif.) into the BglII and EcoR1 sites of the PECE expression vector, Ellis, L., et al. Cell, 45, 721–732 (1986), incorporated herein by reference. To obtain PECE-TRα, a 2 kb EcoR1 fragment of the TRα clone prbeA12, Thompson, C. C., et al., Science, 237, 1610–1613 (1987) incorporated herein by reference was cloned into the EcoR1 site of PECE, Ellis, L., et al., supra. G17-2 CAT was derived from G17-2 Luc, Glass, C. K., et al., supra, by exchange of the reporter gene.

EXAMPLE VII

A RAR-E₂ Hybrid Receptor Confers Estradiol Inducibility to a TRE-CAT Gene

As shown in FIG. 7(a) B1-RAR clone was digested with ApaI and HincII t o remove a 1 kB fragment with the hormone-binding domain and the COOH-terminus of the RARε. A 1.15 kb NaeI-ApaI fragment of the human ER clone B1-ER, Benbrook, D. and Pfahl, M., Science, 238, 788–791 (1987), was ligated to the RARε fragment which encodes the aminoterminal and DNA binding domains. DNA sequencing confirmed the in-frame connection between the RAR DNA binding domain and the ER hinge region. For expression, a 1.8 kb BamHI-SalI fragment from B1-RAR-E₂ was; cloned into the BgII & SalI sites of PECE. F9 cells were cotransfected with 5 μg of PECE-RAR-E₂ and 20 μg of G17-2 CAT or MHC-CAT. As a control, cells were transfected with the reporter plasmid only. Estradiol (E₂) was added 24 hour, after transfection (final concentration $5 \times 10^{-7}$ M). CAT activity was determined as described in Example VI. In the presence of E₂, MHC-CAT is induced two-fold by RAR-E₂ and G17-2 CAT is induced 20 fold (fold induction is calculated from 3 independent experiments) (See FIG. 7b).

EXAMPLE VIII

RARε Activates Transcription from a Thyroid Hormone Responsive Element in CV-1 Cells CV-1 is wire cotransfected with 5 pg of PECE-RARε, PECE-TRα or PECE-Tβ as indicated and 20 μg of G17-2 CAT. Final concentrations of hormone were $6 \times 30^{-7}$ (RA) and $10^{-7}$ (T₃) (See, FIG. 8). Fold activation was determined as the mean of 3 separate experiments.

$1.8 \times 10^6$ CV-1 cells were cultured as monolayers in DMEM (GIBCO, Santa Clara, Calif.), supplemented with 10% FCS. Transfections and assays were as described in Example VI. For construction of PECE-TRβ a 1.6 kb EcoR1 fragment of the human c-erbAβ clone, Weinberger, C., et al., Nature, 324, 641–646 (1986), incorporated herein by reference, was ligated into the EcoR1 site of the PECE vector.

EXAMPLE IX

Thyroid Hormone Receptors Repress the Activity of RARE in F9 and CV-1 Cells

Figure 9A:
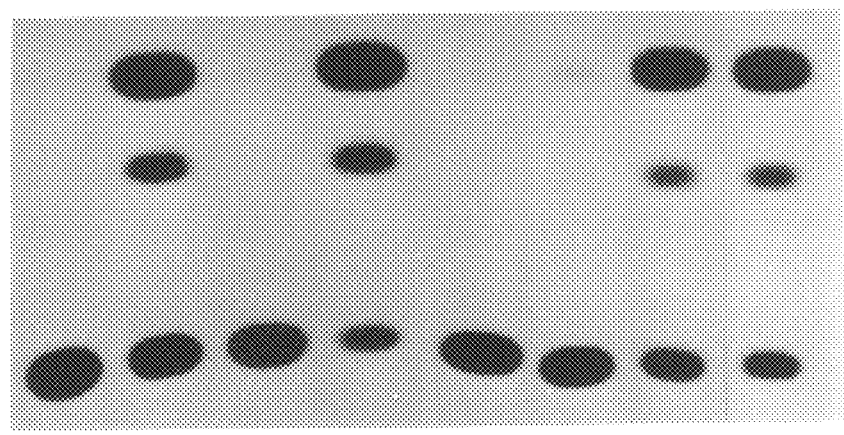
FIGS. 9a and 9b show thyroid hormone receptors repress the activity of RARε in F9 and CV-1 cells.
Figure 9B:
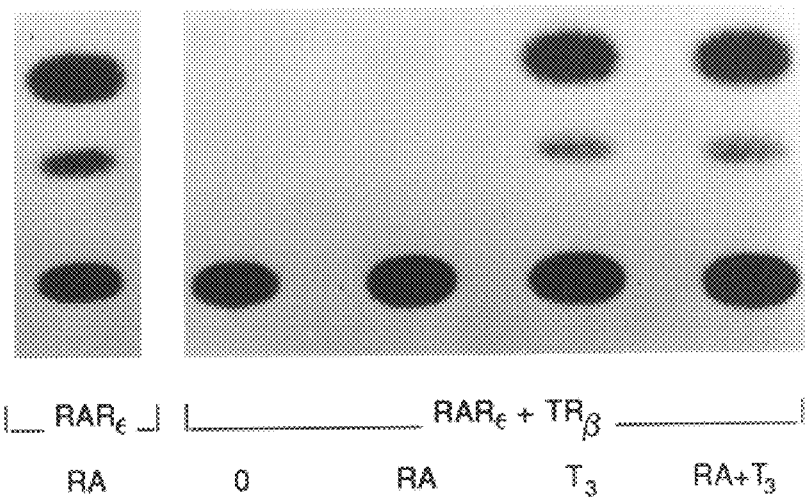

As shown in FIG. 9(a), 5 μg of PECE-RARε plus 5 μg of PECE-TRα were cotransfected together with 20 μg of G17-2 CAT into F9 cells. As a control, each receptor was also cotransfected with G17-2 CAT individually. Hormones were added as indicated. As shown in FIG. 9(b), 2.5 μg of PECE-TRβ plus 2.5 μg of PECE-RARε were cotransfected with 20 μg of G17-2 CAT into CV-1 cells. As a control, PECE-RARε was also cotransfected with G17-2 individually. Hormones were added as indicated. CAT activity was assayed as described in Example VI.

EXAMPLE X

Defining RAR Regions Sensitive to TR Repression By Hybrid Receptor Analysis

As shown in FIG. 10(a), 5 μg of RAR-E₂ plus 5 μg of TRα were cotransfected with 20 μg of G17-2 CAT into F9 cells. As a control, 5 μg RAR-E₂ and 20 μg of G17-2 were also cotransfected individually with the reporter gene. Hormones were added as indicated at concentrations as given above. FIG. 10(b) shows the hybrid receptor RAER-1 contains the ER-DNA binding domain and was previously described, Benbrook, D., et al., (1988), supra. RAER-II contains amino acids 1–287 of the human ER (which includes the DNA binding domain up to the hinge region) and amino acids 169–448 of RAR (which includes a portion of the hinge region and the hormone binding domain). FIG. 10(c) showns RAER-I and RAER-II activate transcription from an ERE-TK-CAT reporter gene in the presence of TRα. CV-1 cells were cotransfected with 2.5 μg of PECE-RAER-I or PECE-RAER-II and 2.5 μg PECE-TRα, together with 20 μg of ERE-TK-CAT reporter gene as described above. The ERE-TK-CAT contains an estrogen responsive element (ERE), Klein-Hitpass, L., et al., Cell 46, 1053–1061 (1986), incorporated herein by reference. Transfected cells were treated with $6 \times 10^{-7}$ M RA, $10^{-7}$ M T₃, or RA+T₃ as indicated.

Although the invention has been described with reference to the presently-preferred embodiment, it should be understood that various modifications can be made without departing from the; spirit of the invention. Accordingly, the invention is limited only by the following claims.

What is claimed is:

1. A method of screening ligands for ligands which stimulate or inhibit RARε comprising adding the ligand to a recombinant host cell containing RARε and observing the stimulation or inhibition of a polypeptide encoded by a reporter gene operably linked to a RARε responsive element, an increase in the polypeptide indicating the stimulation of RARε and a decrease in the polypeptide indicating the inhibition of RARε.

* * * * *